United States Patent [19]

Jadvar et al.

[11] Patent Number: 5,109,851
[45] Date of Patent: * May 5, 1992

[54] MULTIPLE ELECTRODE AFFIXABLE SHEET

[75] Inventors: Hossein Jadvar, Chicago; William T. Metzger, Libertyville, both of Ill.

[73] Assignee: Arzco Medical Systems, Inc., Vernon Hills, Ill.

[ * ] Notice: The portion of the term of this patent subsequent to Dec. 3, 2008 has been disclaimed.

[21] Appl. No.: 650,961

[22] Filed: Feb. 5, 1991

Related U.S. Application Data

[63] Continuation of Ser. No. 306,997, Feb. 6, 1989, Pat. No. 5,069,215.

[51] Int. Cl.⁵ .................. A61B 5/0402; A61B 8/12; A61N 1/05
[52] U.S. Cl. .................. 128/642; 128/660.03; 128/662.06; 128/784; 128/419 P
[58] Field of Search .................. 128/642, 640, 662.06, 128/784, 786, 419 D, 419 P, 660.03

[56] References Cited

U.S. PATENT DOCUMENTS

| 3,568,660 | 3/1971 | Crites et al. ................ 128/786 |
| 3,734,094 | 5/1973 | Calinog . |
| 3,951,136 | 4/1976 | Wall . |
| 4,176,660 | 12/1979 | Mylrea et al. . |
| 4,319,580 | 3/1982 | Colley et al. ................ 128/661.07 |
| 4,476,872 | 10/1984 | Perlin ................ 128/642 |
| 4,640,298 | 2/1987 | Pless et al. . |
| 4,674,518 | 6/1987 | Salo ................ 128/786 X |
| 4,706,681 | 11/1987 | Breyer ................ 128/786 X |
| 4,706,688 | 11/1987 | Michael et al. ................ 128/642 X |
| 4,735,206 | 4/1988 | Hewson . |
| 4,762,135 | 8/1988 | Puije et al. ................ 128/784 |
| 4,763,660 | 8/1988 | Kroll et al. ................ 128/640 |
| 4,817,611 | 4/1989 | Arzbaecher et al. . |
| 4,834,102 | 5/1989 | Schwarzchild et al. . |
| 4,852,580 | 8/1989 | Wood . |
| 4,890,623 | 1/1990 | Cook et al. ................ 128/642 |

FOREIGN PATENT DOCUMENTS

| 121090 | 2/1972 | Fed. Rep. of Germany . |
| 133400 | 1/1979 | Fed. Rep. of Germany . |

OTHER PUBLICATIONS

"A Pill Electrode For . . . Arrhythmia" J Med. Inst. 1978, by R. Arzbaecher.
"Use of the Pill Electrode . . . Pacing" by Jenkins et al, Journal PACE, 1985.

Primary Examiner—Lee S. Cohen
Attorney, Agent, or Firm—Dressler, Goldsmith, Shore, Sutker & Milnamow

[57] ABSTRACT

A single use disposable esophageal electrode structure is formed with a planar sheet body member. The body member carries a plurality of spaced-apart conductive electrode members. A layer of adhesive on the body member can be used to affix it to an esophageal probe. A plurality of conducting members is coupled to the body member. Each of the conducting members is in turn coupled to a respective one of the electrodes. A free end of the conducting members carries an electrical connector for connection to other electrical units.

33 Claims, 2 Drawing Sheets

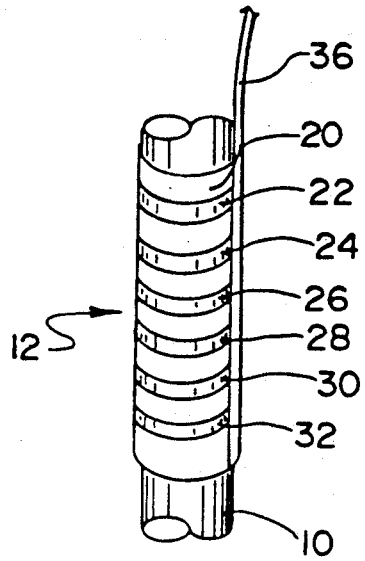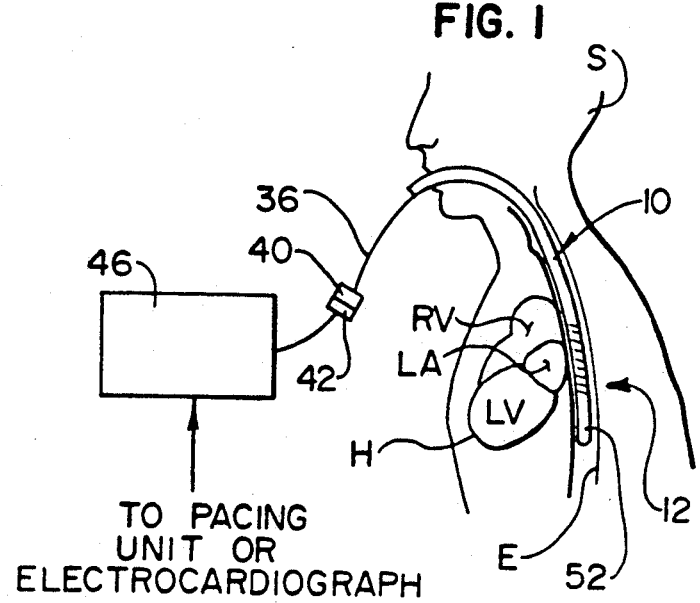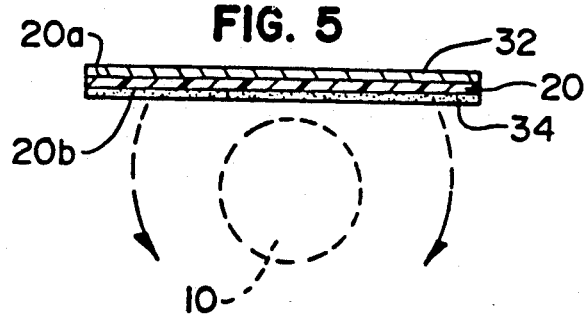

MULTIPLE ELECTRODE AFFIXABLE SHEET

This application is a continuation, of application Ser. No. 306,997, filed Feb. 6, 1989, now U.S. Pat. No. 5,069,215.

FIELD OF THE INVENTION

The invention pertains to noninvasive cardiac sensing or stimulating. More particularly, the invention pertains to an apparatus and a method for noninvasively pacing a subject's heart while simultaneously conducting for cardiac analysis.

BACKGROUND OF THE INVENTION

It has been recognized that esophageal electrodes are particularly useful in connection with noninvasive esophageal pacing. One such electrode is disclosed for example in co-pending and commonly assigned U.S. patent application Ser. No. 930,748 entitled Improved Esophageal Electrocardiography Electrode.

It has also been recognized that transesophageal electrocardiography can be used for the purpose of studying myocardial ischemia. One such system is disclosed in commonly assigned and copending U.S. patent application Ser. No. 267,459 entitled Method and Apparatus For Detection of Posterior Ischemia.

It has also been recognized that transesophageal echocardiography can be utilized for the purpose of detecting or evaluating, among other conditions, myocardial ischemia. It would be desirable to be able to combine the pacing capability of esophageal electrodes and the sensing capability of echocardiography probes into a single unit so as to be able to stress the heart and to simultaneously study its characteristics

SUMMARY OF THE INVENTION

An apparatus and method are provided for esophageal heart pacing or heart monitoring. An apparatus in accordance with the invention has a flexible plastic sheet member. The sheet member, which can be generally of a rectangular shape, carries a plurality of spaced-apart electrode members.

A layer of adhesive is carried on the opposite side of the sheet member from the electrodes. Each of the electrodes is connected to one member of a plurality of insulated wires.

The insulated wires can be formed on an elongated MYLAR sheet member which is affixed at one end to the sheet member. At the other end of the elongated MYLAR sheet member is an electrical connector which is in turn connected to each of the conductors of the sheet member.

The electrical connector can in turn be coupled to a switch for selecting various pairs of electrodes. Outputs from or inputs to the selected pair of electrodes can be coupled to or received from an electrocardiograph or an esophageal pacing unit.

Signals from the esophageal pacing unit can be applied to the selected pair of electrodes for the purpose of noninvasively pacing the heart of the subject. Alternately, signals from the selected pair of electrodes can be provided to an amplifier for further processing for the purpose of driving electrocardiograph.

A method of esophageal pacing using a probe insertable into the esophagus of the subject includes the steps of affixing a disposable plurality of electrodes to the probe; positioning the probe in the esophagus; selecting at least one of the electrodes for pacing; and applying a selected electrical pacing signal to at least the selected electrode.

The present esophageal electrode is especially advantageous in that it can be manufactured as a single use element which can be affixed to a reusable probe prior to use. After use, the electrode unit can be discarded.

Alternately, the present multi-electrode structure could be permanently affixed to an esophageal probe. For example, the present electrode structure could be used with an esophageal ultrasonic probe.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE FIGURES

FIG. 1 is a partial, side, schematic view of a subject illustrating the relationship between a probe in accordance with the present invention and the heart of the subject;

FIG. 2 is an enlarged portion of a probe carrying a multi-element electrode in accordance with the present invention;

FIG. 5 is a sectional view taken along plane 5—5 of FIG. 1; and

DETAILED DESCRIPTION OF THE PREFERRED EMBODIMENT

Figure 3:
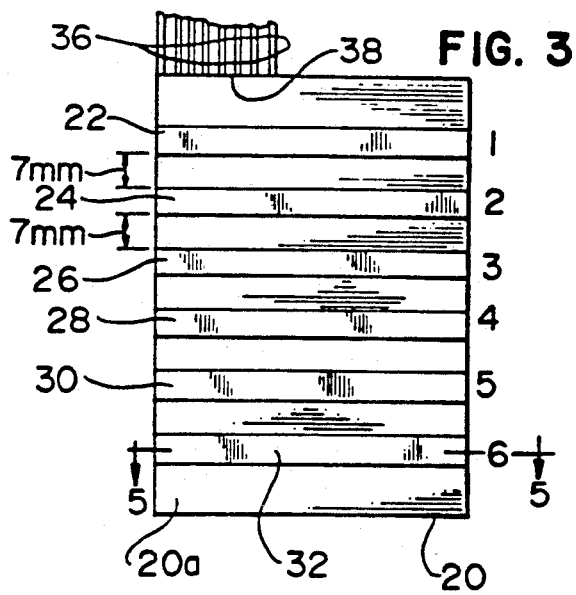
FIG. 3 is an elevational view of one side of a disposable multi-electrode esophageal unit.
Figure 4:
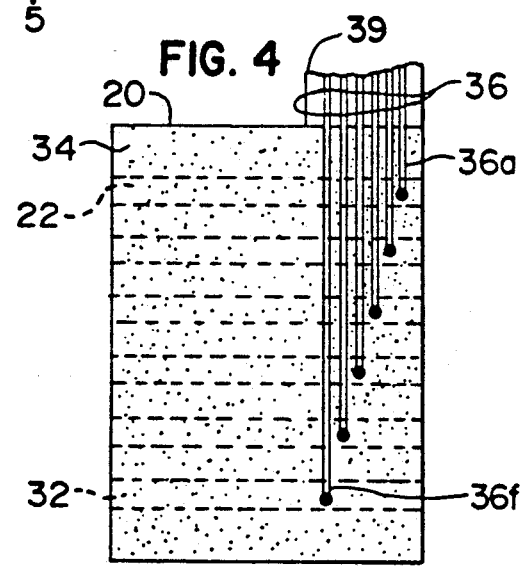
FIG. 4 is a second view of the disposable multi-electrode esophageal unit of FIG. 3.
Figure 6:
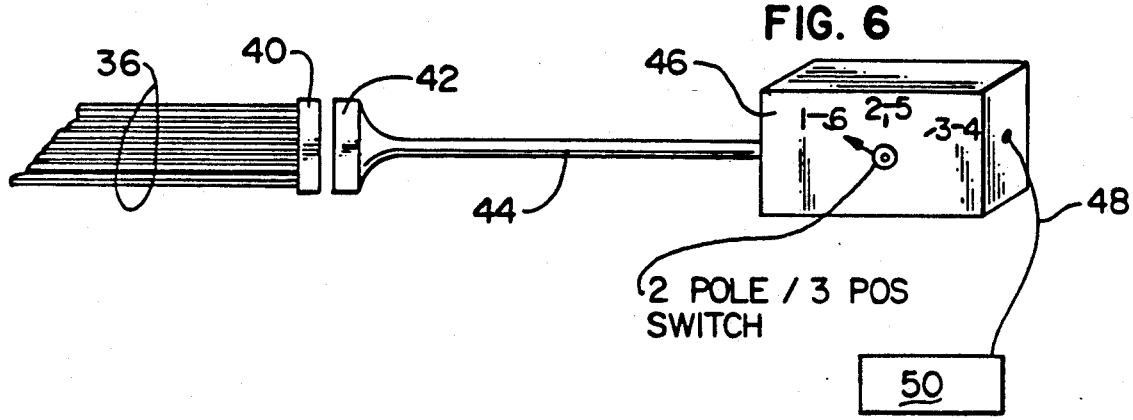
FIG. 6 is a pictorial diagram of an electrode selecting switch in accordance with the present invention.

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

FIG. 1 illustrates a subject S having a heart H and an esophagus E with a probe 10 positioned therein. The probe 10 carries a disposable esophageal electrode structure 12. The structure 12 is formed with a flexible medical grade plastic base member 20. The base member 20 carries a plurality of spaced-apart conducting elements 22-32 on a surface 20a.

Each of the elements 22-32 is formed of a biocompatible conducting material. Each of the elements 22-32 is permanently affixed to the base member 20. The base member 20 on a surface 20b opposite the surface 20a carries a layer of adhesive 34. The layer of adhesive 34 is used to affix the member 20 to the reusable probe 10.

The adhesive layer 34 can be formed of any biocompatible adhesive with adequate strength so as to fix the electrode structure 12 to the probe 10 for the length of any desired procedure. Subsequent to completion of the desired procedure, the electrode structure 12 is removed from the probe 10 and disposed of. The probe 10 can then be sterilized and reused.

A plurality of conducting members 36 is attached in a region 38 to the member 20. The plurality 36 can be formed with a plastic base member 39 on which is deposited a plurality of spaced apart conducting traces 36a-36f. Each of the traces, such as the trace 36a is electrically connected to a respective one of the conducting members 22-32, such as the member 22.

It will be understood that the details of the formation of the traces 36a-36f and the way in which those traces are carried by the plastic member 39 are not limitations of the present invention. Similarly, the details of how the traces 36a-36f interconnect with the conducting members 22-32 are also not a limitation of the present invention.

A second end of the plurality 36 carries an electrical connector 40 of a conventional variety. The connector 40 can be mated with a corresponding connector 42 which is carried by a multiple conductor cable 44. The cable 44 is in turn coupled to a manually operable switch 46.

The switch 46 could for example be implemented as a two-pole three position switch. It will be understood that the exact details of the switch 46 are not a limitation of the present invention. The switch 46 is used to manually select a pair of electrodes from the plurality 22-32. Output from the selected pair of electrodes, or input thereto, on a two-conductor cable 48 can be coupled to an ECG or received from an esophageal pacing unit 50.

The disposable multi-electrode element 12, in combination with the probe 10, makes it possible to combine cardiac pacing as a form of stress simultaneously with echocardiography to determine and sense heart function. For example, if the probe 10 is a transesophageal ultrasonic probe of a type marketed by Hoffrel Instruments, Inc., Model 482, the electrode structure 12 can be used for pacing the left atrium of the heart H. Simultaneously, an ultrasonic transmitter and receiver 52 on the probe 10 transmits ultrasonic waves toward the heart H and senses ultrasonic reflections therefrom for the purpose of forming an image of the cardiac chambers as the heart H is being simultaneously stimulated.

In a typical procedure, the sheet electrode member 12 is affixed to the perimeter of the probe 10 using the layer of adhesive 34. The electrode structure 12 is located at a level about 10 centimeters above the ultrasonic transmitter and receiver 52 in the probe.

The ultrasonic transmitter/receiver 52 is carried at a distal end of the probe 10. The multi-electrode element 12 is carried on the probe 10 adjacent the transmitter/receiver 52 but spaced therefrom.

The probe 10 is inserted in a conventional fashion into the esophagus E of the subject S. The electrode structure 12 is then connected via connectors 40, 42 to switch selector 46. The appropriate electrodes are selected and then either an esophageal preamplifier or a pacing unit is coupled to the cable 48 for sensing signals from or for pacing the heart H.

By way of example and not by way of limitation, the width of each of the electrode members 22-32 can be on the order of 7 millimeters with a corresponding spacing therebetween. The length dimension of the sheet member 20 can be on the order of 63 millimeters and the width dimension can be on the order of 40 millimeters.

The length of the plastic extension member 40, which could be formed of MYLAR can be on the order of 50 centimeters. The body member 20 can also be formed of a MYLAR sheet. It will be understood that any medical grade plastic could be used for the body member 20 without departing from the spirit and scope of the present invention.

Further, in a typical installation the switching unit 46 can be connected so as to switch as electrode pairs, electrodes 22, 32; 24, 30; or 24,26.

Alternately, the multiple electrode system 12 can be fabricated permanently attached to an imaging probe. Imaging probes, of the type discussed above, usually include an ultrasonic transmitter and receiver located at the end of the probe.

The transmitter is located in the esophagus below the heart and is oriented on the probe to transmit toward the heart. Reflected ultrasonic waves are detected by the transceiver, converted to corresponding electrical signals and transmitted from the probe to outside analysis circuitry.

Hence, it will be understood that the multiple electrodes 22-32 could be permanently attached to the body of the esophageal ultrasonic probe as generally indicated in FIG. 1.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A multi-element electrode structure affixable to an essentially cylindrical esophageal probe which can then be inserted into the esophagus of a patient, the electrode structure comprising:

a rectangular insulative sheet member having a selected length dimension, a width dimension and wrappable on the esophageal probe;

means, carried by said sheet member, for removably affixing said member to the probe;

a plurality of spaced, conducting electrode members carried by said sheet member; and a plurality of elongated conducting members with each said conducting member having an end in electrical contact with a respective one of said electrode members.

2. A multi-element electrode structure as in claim 1 with said plurality of elongated conducting members carrying an electrical connector displaced from said sheet member.

3. A multi-element electrode structure as in claim 2 including means, couplable to said connector, for electrically selecting at least one of said electrode members.

4. A multi-element electrode structure as in claim 2 including means for electrically selecting at least first and second of said electrode members.

5. A multi-element electrode structure as in claim 1 with said sheet member formed of a selected plastic.

6. A multi-element electrode structure as in claim 1 with said affixing means including adhesive.

7. A method of non-invasively pacing the heart of a subject comprising:

providing a reusable esophageal probe with an exterior housing;

removably affixing a disposable plurality of singleuse electrodes to the exterior housing of the probe;

positioning the probe in the esophagus;

selecting at least one of the electrodes; and applying, using the selected electrode, pacing electrical signals to the heart.

8. A method as in claim 7 including removing the probe from the esophagus and then removing the plurality of electrodes from the housing of the probe.

9. A method as in claim 7 including:
carrying out a heart imaging function during the pacing step.

10. A probe usable to non-invasively pace the heart of a subject comprising:
an elongated body portion having a proximal end and a distal end;
at least a transmitter carried on said distal end;
a plurality of spaced-apart electrodes carried on said body portion between said proximal end and said transmitter but spaced therefrom thereby providing the independent positioning of said transmitter with respect to the subject's heart and for independent selection of a pacing electrode for pacing the heart.

11. A probe as in claim 10 with said plurality of electrodes removably attached to said body portion.

12. A probe as in claim 10 including adhesive located adjacent to at least some of said electrodes for retaining said electrodes on said body portion.

13. A probe as in claim 10 with at least some of said electrodes having a generally rectangular shape.

14. A probe as in claim 10 connectable to an external electrical device and including means, coupled to said transmitter and extending substantially to said proximal end of said body portion, for connection to the external electrical device.

15. A probe as in claim 10 including a receiver carried on said distal end of said body portion.

16. A probe as in claim 10 including means for electrical conduction coupled to at least some members of said plurality of electrodes and extending to said proximal end of said body portion.

17. A probe as in claim 10 including a connector spaced from but electrically coupled to said electrodes.

18. A method of cardiac imaging of a subject using a multi-function esophageal probe which carries at least an imaging receiver at a distal end thereof and a plurality of electrodes adjacent to but spaced from the receiver, the method comprising:
inserting the distal end into the esophagus of the subject;
locating the receiver to carry out a selected imaging function;
selecting at least one pacing electrode from among the members of the plurality of electrodes; and
providing pacing electrical signals to the selected electrode while simultaneously carrying out the imaging function.

19. A cardiac imaging probe comprising:
an elongated body portion having a proximal end and a distal end;
an ultrasonic imaging receiver carried on said distal end;
a plurality of spaced-apart pacing electrodes carried by said body portion adjacent to said receiver but spaced therefrom toward said proximal end with said plurality of electrodes and said body portion coupled together and with at least a first electrode independently selectable from said plurality to carry out a heart pacing function simultaneously with said imaging receiver carrying out a heart imaging function.

20. A probe as in claim 19 with said plurality of electrodes removably coupled to said body portion.

21. An esophageal probe as in claim 40 with said plurality of electrodes adhesively coupled to said body portion.

22. A probe as in claim 19 including manually adjustable means, couplable to said proximal end of said body portion, for selecting said first and a second pacing electrode from said plurality of electrodes.

23. A probe comprising:
an elongated body having a proximal end and a distal end;
an imaging element carried on said distal end;
a plurality of spaced-apart electrodes usable for cardiac pacing supported on said body adjacent to but spaced from said imaging element toward said proximal end; and
means for electrically coupling to at least one of said electrodes for carrying out a cardiac imaging function simultaneously with a pacing function.

24. An esophageal probe for use in imaging and pacing an individual's heart, the probe comprising:
an elongated body having a proximal end and a distal end;
a heart imaging element carried on said body located adjacent to said distal end; and
a plurality of electrodes carried by said body and located between said proximal end and said imaging element, adjacent to but spaced from said element, each of said electrodes being located at a different distance from said element, such that when said element is properly positioned for imaging, at least one of said electrodes will be properly positioned for pacing the heart.

25. A probe as in claim 24 with said plurality of electrodes removably attached to said body.

26. A probe as in claim 24 including a flexible base member disposed between said body and said electrodes and including adhesive carried on at least a portion of said base member for removably affixing said base member and said electrodes to said body.

27. A probe assembly kit comprising a reusable elongated probe having distal and proximal ends and an outer surface located between said ends, said probe including an imaging transceiver located adjacent to said distal ends, and a plurality of attachable electrode assemblies each including a plurality of spaced electrodes, means for removably affixing one of said electrode assemblies to said outer surface of said probe such that said one of said electrode assemblies may be removed from said probe after use and replaced with another one of said electrode assemblies.

28. A probe assembly kit as in claim 27 with each of said electrode assemblies including a planar, flexible plastic sheet member with a respective plurality of electrodes carried thereon.

29. A multi-element electrode structure removably affixable to an essentially cylindrical esophageal probe which can then be inserted into an esophagus of a patient, the electrode structure comprising:
an insulative sheet member;
a plurality of spaced electrodes carried by said sheet member;
means for removably affixing said sheet member to the probe such that at least some of said electrodes substantially encircle said probe; and
a plurality of elongated conducting members with each of said conducting members having an end in electrical contact with a respective one of said electrodes.

30. A multi-element electrode structure as in claim 29 with said plurality of elongated conducting members carrying an electrical connector displaced from said sheet member.

31. A multi-element electrode structure as in claim 29 with said sheet member formed of a plastic.

32. A multi-element electrode structure as in claim 29 with said affixing means including adhesive.

33. A dual mode probe for stimulating and imaging a selected organ when located proximate thereto comprising:

a body with a first and a second end;

an organ imaging element carried on said body adjacent to said second end;

a plurality of electrodes carried by said body and located between said first end and said imaging element, adjacent to but spaced from said element, each of said electrodes being located at a different distance from said element, such that when said element is properly positioned for imaging, at least one of said electrodes will be properly positioned for stimulating the organ.

* * * * *

UNITED STATES PATENT AND TRADEMARK OFFICE
CERTIFICATE OF CORRECTION

PATENT NO. : 5,109,851

DATED : May 5, 1992

INVENTOR(S) : Jadvar et al.

It is certified that error appears in the above-identified patent and that said Letters Patent is hereby corrected as shown below:

Column 5, line 15, change "the" to --for--.

Signed and Sealed this

Twenty-fourth Day of August, 1993

Attest:

BRUCE LEHMAN

Attesting Officer

Commissioner of Patents and Trademarks